(12) United States Patent
Clayton

(10) Patent No.: US 11,712,585 B2
(45) Date of Patent: Aug. 1, 2023

(54) SYSTEMS, METHODS, AND DEVICES FOR HIGH-ENERGY IRRADIATION

(71) Applicant: VARIAN MEDICAL SYSTEMS, INC., Palo Alto, CA (US)

(72) Inventor: James E. Clayton, San Jose, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 17/983,452

(22) Filed: Nov. 9, 2022

(65) Prior Publication Data

US 2023/0069176 A1   Mar. 2, 2023

Related U.S. Application Data

(63) Continuation of application No. 17/106,506, filed on Nov. 30, 2020, now Pat. No. 11,547,873, which is a continuation of application No. 16/274,681, filed on Feb. 13, 2019, now Pat. No. 10,912,952, which is a continuation of application No. 14/862,864, filed on Sep. 23, 2015, now Pat. No. 10,252,083.

(51) Int. Cl.
*A61N 5/10* (2006.01)

(52) U.S. Cl.
CPC .... *A61N 5/1067* (2013.01); *A61N 2005/1055* (2013.01); *A61N 2005/1088* (2013.01); *A61N 2005/1089* (2013.01)

(58) Field of Classification Search
CPC .......... A61N 5/1067; A61N 2005/1055; A61N 2005/1089
See application file for complete search history.

(56) References Cited

U.S. PATENT DOCUMENTS

| 4,570,103 A | 2/1986 | Schoen |
| 5,602,894 A | 2/1997 | Bardash |
| 6,198,957 B1 | 3/2001 | Green |

(Continued)

OTHER PUBLICATIONS

Bielajew, Alex F., "The effect of strong longitudinal magnetic fields on dose deposition from electron and photon beams," Medical Physics, 1993, 20: 1171-79.

(Continued)

*Primary Examiner* — Chih-Cheng Kao
(74) *Attorney, Agent, or Firm* — Potomac Law Group, PLLC

(57) ABSTRACT

A high-energy radiation treatment system can comprise a laser-driven accelerator system, a patient monitoring system, and a control system. The laser-driven accelerator system, such as a laser-driven plasma accelerator or a laser-driven dielectric microstructure accelerator, can be constructed to irradiate a patient disposed on a patient support. The patient monitoring system can be configured to detect and track a location or movement of a treatment volume within the patient. The control system can be configured to control the laser-driven accelerator system responsively to the location or movement of the treatment volume. The system can also include a beam control system, which generates a magnetic field that can affect the radiation beam and/or secondary electrons produced by the irradiation beam. In some embodiments, the beam control system and the patient monitoring system can comprise a magnetic resonance imaging system.

20 Claims, 8 Drawing Sheets

(56) References Cited

U.S. PATENT DOCUMENTS

| | | |
|---|---|---|
| 6,862,469 B2 | 3/2005 | Bucholz et al. |
| 8,331,531 B2 | 12/2012 | Fahrig et al. |
| 10,252,083 B2 | 4/2019 | Clayton |
| 10,912,952 B2 | 2/2021 | Clayton |
| 2002/0090194 A1 | 7/2002 | Tajima |
| 2002/0153893 A1 | 10/2002 | Watkins et al. |
| 2004/0104354 A1 | 6/2004 | Haberer et al. |
| 2005/0197564 A1* | 9/2005 | Dempsey ............. A61B 5/4836 600/411 |
| 2006/0262905 A1 | 11/2006 | Reiffel |
| 2007/0055144 A1 | 3/2007 | Neustadter et al. |
| 2008/0292054 A1 | 11/2008 | Rosengren et al. |
| 2008/0298401 A1 | 12/2008 | Faure et al. |
| 2009/0149735 A1 | 6/2009 | Fallone et al. |
| 2011/0012593 A1 | 1/2011 | Shvartsman et al. |
| 2011/0017920 A1 | 1/2011 | Goer et al. |
| 2011/0105821 A1 | 5/2011 | Dieter et al. |
| 2011/0200170 A1 | 8/2011 | Nord et al. |
| 2011/0218420 A1* | 9/2011 | Carlone ............... A61N 5/1049 600/411 |
| 2011/0260729 A1 | 10/2011 | Carlone et al. |
| 2013/0259198 A1 | 10/2013 | Alezra et al. |
| 2014/0135563 A1 | 5/2014 | Loo et al. |
| 2014/0294154 A1* | 10/2014 | Slatkin ................ A61N 5/1042 378/65 |
| 2019/0175940 A1* | 6/2019 | Hissoiny ............. A61N 5/1039 |

OTHER PUBLICATIONS

Litzenberg et al., "An apparatus for applying strong longitudinal magnetic fields to clinical photon and electron beams," Physics in Medicine and Biology, 2001, 46: pp. N105-15.

Raaijmakers et al., "Integrating a MRI scanner with a 6 MV radiotherapy accelerator: dose increase at tissue-air interfaces in a lateral magnetic field due to returning electrons," Physics in Medicine and Biology, 2005, 50: pp. 1363-1376.

* cited by examiner

SYSTEMS, METHODS, AND DEVICES FOR HIGH-ENERGY IRRADIATION

FIELD

The present disclosure relates generally to radiotherapy or radio-surgical treatments, and, more particularly, to high-energy irradiation (e.g., electron or photon beams), such as from laser-driven accelerators, for treatment of cancers.

BACKGROUND

Lung cancer is the leading cause of cancer deaths in the United States. It claims more lives than colon, prostate and breast cancer combined. Over 196,000 patients are diagnosed with lung cancer each year in the United States and nearly 160,000 die of it. Yet, lung cancer patients are poorly serviced by current treatment protocols. Radiation therapy is a well-known option for the treatment of certain cancers, where ionizing radiation is directed to control or kill cancer cells (i.e., a malignant tumor) while limiting damage to healthy tissue. However, the treatment of lung cancers (and other cancers) may present an issue, for example, when the tumors move during irradiation.

Due to breathing by the patient, cancerous tumors within the lung are constantly in motion. Moreover, lung tissue is very sensitive to radiation, and damage can readily occur to healthy tissue surrounding the tumors within the lung. Often these tumors are found only once they are of substantial size (e.g., greater than 3 cm in diameter), such that patients are already quite ill when treatment begins. Since the tumor moves with each breath the patient takes, existing irradiation techniques generally increase the irradiation volume to account for this motion, thereby exposing increasing amounts of healthy tissue to potentially damaging radiation.

In image guided radiation therapy (IGRT), the radiation is guided to the treatment site based on images of the patient or surrogates attached to the patient. But since cancerous tumors in the lung are constantly moving due to breathing, precise targeting for IGRT proves to be a challenge. A new treatment modality for treating lung cancer, and other cancers where tumor motion may be an issue, is still needed.

SUMMARY

Systems, methods, and devices for treatment by high-energy irradiation are disclosed herein. In one or more embodiments, a laser-driven accelerator, such as a laser-driven plasma accelerator or a laser-driven dielectric microstructure accelerator, can generate a pulsed beam of electrons having energy of at least 50 MeV or a pulsed photon beam of X-rays having energy of at least 10 MeV. A treatment volume within the patient can be monitored contemporaneously with or in between pulses of the radiation beam. The radiation beam can then be redirected to account for any change in location of the treatment volume, or the irradiation may be timed such that a static location of the radiation beam coincides with the location of the moving treatment volume. Because each pulse of the radiation beam is much shorter than any potential patient motion (e.g., due to patient breathing), any difference between the monitored location of the treatment volume and the actual location of the treatment volume during irradiation times by the radiation beam can be minimized, or at least reduced.

In some embodiments, the radiation beam is an electron beam with an initial beam diameter less than 200 µm. Transverse growth of the electron beam as it enters the patient can be controlled using a longitudinal magnetic field, for example, from a magnetic resonance imaging (MRI) system or a solenoid. The well-controlled electron beam focal spot size and/or the short pulse timing and treatment volume monitoring may allow for irradiation of moving treatment volumes within a patient while minimizing, or at least reducing, damage to potentially healthy tissue or other critical structures.

In some embodiments, a magnetic field, for example, from an MRI system or a solenoid, can be used to control secondary electrons generated within the body of the patient. Secondary electrons can be produced during irradiation by the radiation beam (e.g., high-energy primary electrons or photons) and contribute to the dose received by the patient. A longitudinal magnetic field (i.e., parallel to the axis of the radiation beam) may assist with focusing the secondary electrons at the intended treatment volume. Alternatively or additionally, a transverse magnetic field (i.e., perpendicular to the axis of the radiation beam) may cause secondary electrons exiting the treatment volume to be redirected back to the treatment volume.

In one or more exemplary embodiments of the disclosed subject matter, a treatment system can comprise a laser-driven accelerator system, a patient monitoring system, and a control system. The laser-driven accelerator system can be constructed to irradiate a patient disposed on a patient support, for example, electrons having energies of at least 50 MeV or X-ray photons having energies of at least 10 MeV. The patient monitoring system can be configured to detect and track a treatment volume within the patient. The control system can be configured to control the laser-driven accelerator system responsively to a location or movement of the treatment volume tracked by the patient monitoring system.

In one or more exemplary embodiments, a high-energy electron treatment method comprises generating a radiation beam, for example, comprising electrons having energies of at least 50 MeV or X-ray photons having energies of at least 10 MeV, using a laser-driven accelerator system. The method can also include detecting and tracking a location and/or movement of a treatment volume within a patient disposed on a patient support, and irradiating the patient with pulses of the radiation beam responsively to the tracked location and/or movement of the treatment volume.

In one or more exemplary embodiments, a non-transitory computer-readable storage medium upon which is embodied a sequence of programmed instructions for controlling a treatment system to irradiate a patient is provided. The computer processing system can execute the sequence of programmed instructions embodied on the computer-readable storage medium to track a location and/or movement of a treatment volume within a patient disposed on a patient support, and to send a control signal to a laser-driven accelerator system to generate a radiation beam that irradiates the patient responsively to the tracked location and/or movement of the treatment volume.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

In one or more embodiments of the disclosed subject matter, a pulsed beam of high-energy radiation (e.g., electrons or other particles having an energy of at least 50 MeV, for example, in a range from 50-300 MeV, or X-ray photons having an energy of at least 10 MeV) can be generated from a laser-driven accelerator system (e.g., a laser-driven plasma accelerator or a laser-driven dielectric microstructure) and used to treat tumors of various sizes. When using electrons, the resulting pulsed radiation beam can have a sub-millimeter spot size (e.g., less than 200 μm, for example, 20-200 μm), and thus may be considered a pencil beam of electrons that precisely targets a tumor within a patient. The relatively short timing of each pulse (e.g., less than 100 fs, for example, 20-100 fs) as compared to the timing of patient motion (e.g., on the order of milliseconds) allows for negligible or minimal change in the location of the treatment volume during irradiation. The location and/or movement of the treatment volume can be tracked, for example, using a magnetic resonance imaging (MRI) system or other medical imaging system, and each pulse of the radiation beam controlled based on the tracked location and/or movement to follow the desired treatment volume despite any change in location or such that the patient is only irradiated when the location of the desired treatment volume coincides with an axis of the radiation beam.

The MRI system (or a separate system) can be used to generate longitudinal magnetic fields that limit the transverse growth of the pulsed electron beam as it propagates, thereby reducing the likelihood of damage to otherwise healthy tissue or other critical structures surrounding the treatment volume. The longitudinal magnetic field may also serve to focus any secondary electrons generated by the interaction of the radiation beam (either a particle beam or X-ray photon beam) onto to the treatment volume, thereby increasing the dose received. Alternatively or additionally, an externally applied magnetic field, such as from a solenoid, can be used to limit the transverse growth of the pulsed electron beam. In other configurations, the MRI system or a separate system can be used to generate transverse magnetic fields that redirect secondary electrons from the treatment volume back onto the treatment volume, thereby increasing the dose received. Embodiments of the disclosed treatment system can be used as a surgical tool for stereotactic body radiation therapy (SBRT) or stereotactic ablative radiotherapy (SABR), or hypo-fractionated radiotherapy procedures among other therapies.

Figure 1A:
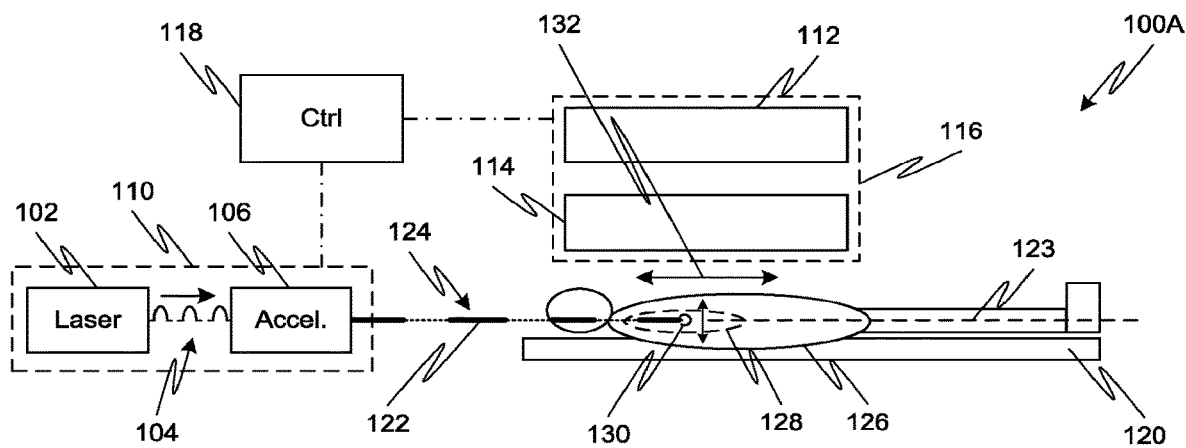
FIG. 1A shows a treatment system employing a laser-driven accelerator to irradiate a patient with a high-energy electron beam, according to one or more embodiments of the disclosed subject matter.

Referring to FIG. 1A, an embodiment of a high-energy electron treatment system 100 is shown. The treatment system 100 can include a laser-driven accelerator system 110. In the accelerator system 110, a laser 102 drives an electron accelerator 106. For example, the electron accelerator 106 can be a plasma accelerator driven by Wakefield laser pulses 104 from laser 102, for example a Ti:sapphire laser. In such an arrangement, a chamber of the accelerator 106 includes a low density gas therein, which is ionized upon exposure to a laser pre-pulse (either from laser 102 or another laser (not shown)) or an electrical discharge. A laser focusing device (not shown) focuses each Wakefield laser pulse 104 (e.g., a sub-picosecond laser pulse) into the gas-filled chamber, each laser pulse 104 acting to push electrons in the plasma off of their respective nuclei to form an electron beam 124 with discrete pulses 122. Each pulse 122 of electrons may be on the order of femtoseconds, e.g., less than 100 fs. In another example, the electron accelerator 106 can include a fused quartz grating to which the laser 102 provides sub-picosecond laser pulses. In another example, the plasma accelerator can be a dielectric microstructure (i.e., an accelerator on a chip) that produces electrons from laser pulses 104. Other types of laser-driven accelerators that generate high-energy electrons are also possible according to one or more contemplated embodiments.

The pulsed electron beam 124 can be directed from the accelerator 106 along an irradiation direction or axis 123 toward a treatment volume 130 within an organ 128 (e.g., the thorax, lung, head, or neck) of a patient 126 held on a patient support 120. The treatment volume 130 may be subject to motion within the patient 126, for example, due to motion of the patient 126 or motion of the organ 128 within the patient 126 (e.g., breathing-induced motion). Such motion of treatment volume 130 may be on the order of milliseconds or seconds. Thus, each pulse 122 of the electrons delivered to the patient 126 may be while the treatment volume 130 is considered to be substantially stationary (or with negligible change in location) during the time period of the pulse and while the locations of the irradiation axis 123 and the treatment volume 130 coincide. Since an individual pulse from the laser-driven accelerator system 110 is fast (e.g., on the order of 5-100 femtoseconds), the pulse repetition rate can be on the order of a few hundred Hz to a few kHz thereby enabling efficient delivery of each dose fraction to the treatment volume.

The location of the treatment volume 130 can be monitored during irradiation with each electron pulse 122, or at least prior to a dose fraction comprising one or more electron pulses 122, and irradiation of the patient can be adjusted responsively thereto. For example, a monitoring system 112 can be provided as part of treatment system 100. The monitoring system 112 can image the treatment volume 130 within patient 126 and determine or track the location of the treatment volume and/or changes to the location over time via image processing. The results of the monitoring by system 112 can be communicated to a system controller 118, which can control (i.e., by sending one or more control signals) the accelerator system 110 and/or a moveable support of the accelerator system (not shown) to re-position the electron beam 124 with respect to the changed location of the treatment volume 130. For example, the electron beam 124 can be steered or have its spot size modified to follow the treatment volume (or portions thereof) despite motion of the treatment volume. Alternatively or additionally, the system controller 118 can control the accelerator system 110 such that the patient 126 is only irradiated when the treatment volume 130 is located along the irradiation axis 123 of the stationary electron beam 124. The control system 118 can also coordinate the timing of imaging by the monitoring system 112, laser pulse generation by laser 102, and/or electron beam irradiation from accelerator 106.

Figure 2A:
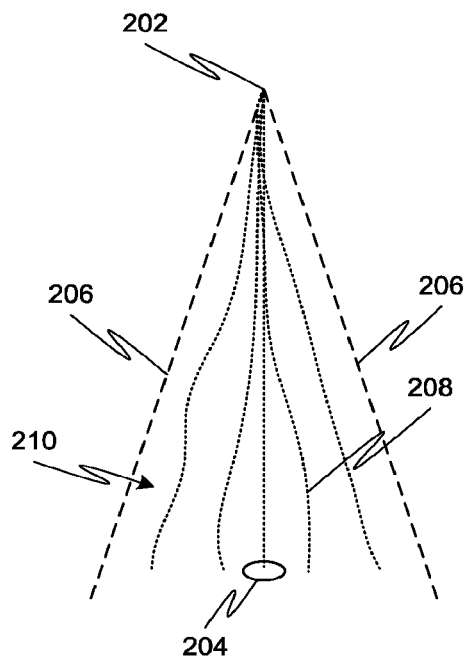
FIG. 2A illustrates the spread of an electron beam and a sample of electron beam paths from a laser-driven accelerator without magnetic field focusing.
Figure 2B:
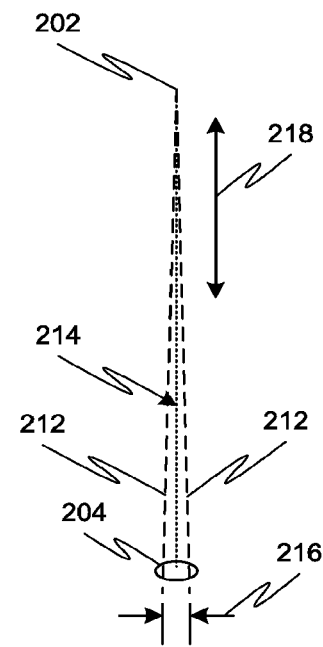
FIG. 2B illustrates the spread of an electron beam and a sample of electron beam paths from a laser-driven accelerator with focusing by a longitudinal magnetic field, according to one or more embodiments of the disclosed subject matter.

The transverse growth of the electron beam 122 as it travels from the accelerator system 110 to the treatment volume 130 can be limited by the use of a longitudinal magnetic field (i.e., along direction 132, which is parallel to irradiation axis 123) from beam control system 114. Referring to FIG. 2A, electrons originating at 202 may progress along respective random pathways 208 between the origin 202 and the desired treatment volume 204, thereby resulting in an electron beam 210 defined by an expanding transverse beam width 206. However, by applying an appropriate longitudinal magnetic field (i.e., in a direction 218 parallel to the irradiation direction of the electron beam), e.g., using beam control system 114, the resulting electron beam 214 can have electron pathways bounded by a substantially reduced transverse beam width 212, as illustrated in FIG. 2B. For example, the beam control system 114 can deliver a magnetic field greater than 1 T, for example, in a range from 1 T to 10 T (e.g., 3 T-6 T or greater than 6 T).

The electron beam can be focused to have a spot size 216 at the treatment volume 204 less than 200 μm, for example, in a range from 20 μm to 200 μm. The electron beam 124 may be sufficient to deliver a charge of at least 1 nC/pulse (i.e., 1 nC per pulse 122). Within the electron beam 124, the pulses can be repeated at a frequency of, for example, at least 10 Hz, and preferably, greater than 250 Hz, for example, on the order of a few kHz. The electron beam 124 can thus deliver dose rates greater than 0.5 Gy/s, for example, in a range from 0.5 Gy/s to 50 Gy/s, depending on the depth and size of the treatment volume (e.g., the tumor).

Figure 2C:
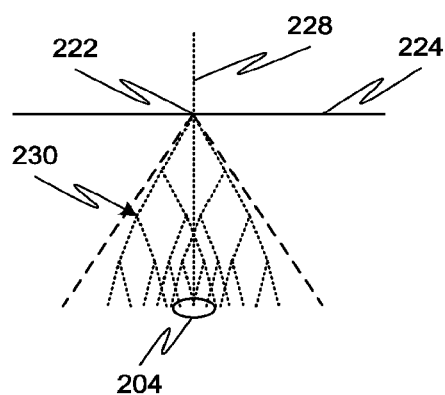
FIG. 2C illustrates the spread of secondary electrons with respect to a treatment volume without magnetic field focusing.
Figure 2D:
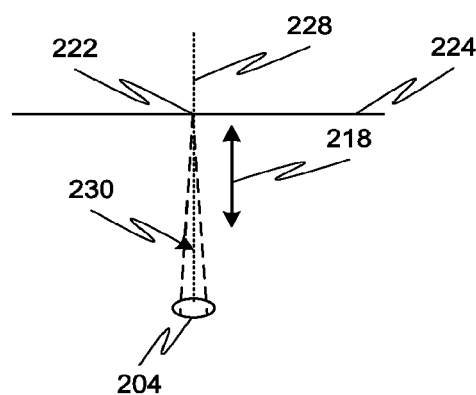
FIG. 2D illustrates the spread of secondary electrons with respect to a treatment volume with focusing by a longitudinal magnetic field, according to one or more embodiments of the disclosed subject matter.

The longitudinal magnetic field can also be used to reduce the spread of secondary electrons generated by the interaction of the primary electrons in the electron beam 112 with the tissue of the patient. Referring to FIG. 2C, an electron beam 228 enters the patient 224 at an origin 222. Because of the high energy of the primary electrons in the electron beam, secondary electrons can be formed within the patient, which secondary electrons may also have sufficient energy to form additional secondary electrons, thereby forming a network 230 of randomly progressing electrons that deliver an irradiation dose to regions of the patient besides the desired treatment volume 204. However, by applying an appropriate longitudinal magnetic field (i.e., in a direction 218 parallel to the irradiation direction of the electron beam 228), e.g., using beam control system 114, the spread of the resulting network 230 of secondary electrons can be reduced so as to focus on the treatment volume 204, as illustrated in FIG. 2D. In one or more embodiments, the beam control system 114 and the monitoring system 112 may be part of a magnetic field generation system 116. For example, magnetic field generation system 116 can comprise an MRI system, wherein the single system provides both beam control and monitoring aspects during different times during a single treatment period.

Figure 3:
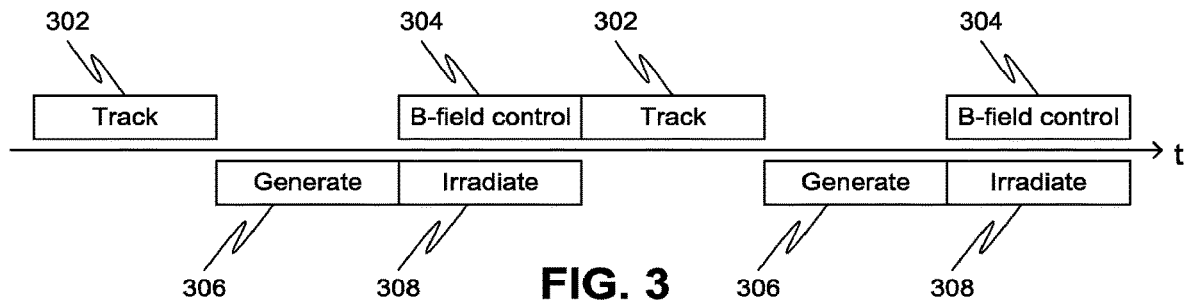
FIG. 3 illustrates timing of treatment volume monitoring, magnetic field focusing, and electron irradiation in a high-energy electron treatment system, according to one or more embodiments of the disclosed subject matter.

Referring to FIG. 3, for example, the monitoring system 112 can perform detection of the treatment volume 130 during a monitoring time period 302. Once the electrons are created in the accelerator system 110, any magnetic field present may negatively influence their trajectory. Accordingly, the monitoring period 302 may terminate immediately before electrons are generated during period 306. Alternatively, the monitoring period 302 may overlap with the period of electron generation 306. However, since the laser-driven accelerator 106 can be relatively small and located closer to the treatment area (e.g., less than 1 m), the amount of deflection caused by the magnetic field can be minimized, or at least reduced.

In yet another alternative, the monitoring system 112 can comprise a non-magnetic medical imaging system, such as, an X-ray imaging system, a nuclear imaging system, an ultrasound imaging system, an optical imaging system, or an infrared imaging system. With such a non-magnetic medical imaging system, the monitoring period 302 may extend throughout the generation period 306, irradiation period 308, and magnetic field control period 304, without impacting the resulting radiation beam.

Once one or more pulses 122 of electrons are generated, they may be directed to the patient during irradiation period 308. Simultaneous with the irradiation 308, a magnetic field may be generated by beam control system 114 to control a transverse spread of the electron beam pulse 122. The time period of the irradiation 308 and the magnetic field control 304 may coincide, while the monitoring period 302 may be subsequent to and/or follow each irradiation period 308. For example, the monitoring period 302 may occur prior to electron beam delivery (i.e., irradiation 308, which may have a time on the order of 10-100 fs for a series of one or more pulses of electrons). The monitoring after the irradiation 308 would then check the location of the treatment volume for the next series of electron pulses.

Alternatively or additionally, the monitoring period 302 can precede and at least partially extend into the electron generation period 306. For example, the monitoring period 302 may overlap with a laser pulse initiation portion of the generation period 306, but terminate prior to an electron beam formation portion of the generation period 306. In another alternative, the monitoring period 302 can precede and overlap with the generation period 306, where any influence of the magnetic field on the generated electron can be mitigated by an appropriate compensation device, such as cancelation coils, or by appropriate positioning of the magnetic generation system 116 with respect to plasma accelerator 106.

Alternatively or additionally, the monitoring during monitoring period 302 can employ predictive tracking and adjust dose delivery to compensate for predicted changes in target location. The predictive tracking may use template matching, for example, as described in U.S. Pat. No. 9,008,398, entitled "Template Matching Method for Image-Based Detection and Tracking of Irregular Shaped Targets," the contents of which are hereby incorporated by reference herein. Other predictive tracking techniques, in addition to or in place of real-time monitoring, may also be used according to one or more contemplated embodiments.

Figure 1B:
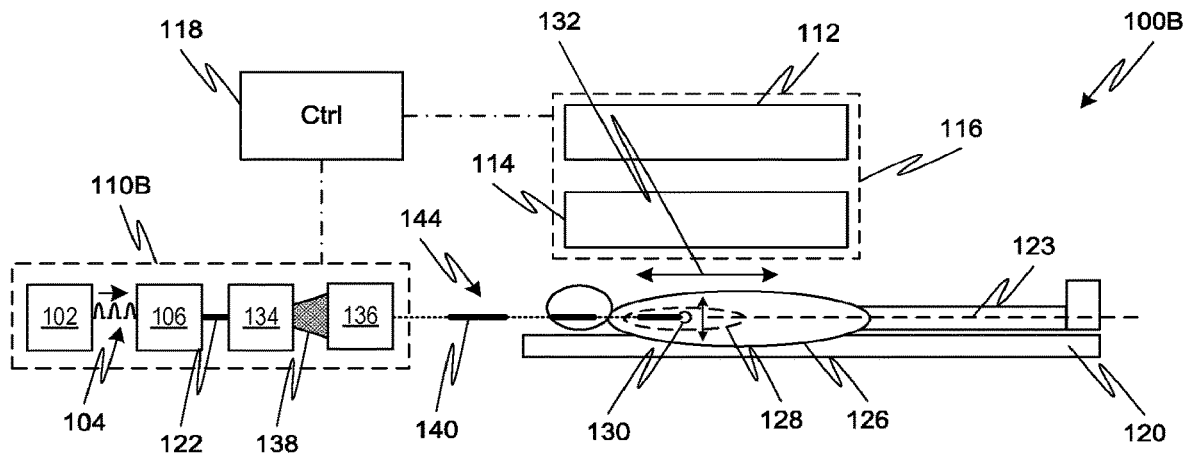
FIG. 1B shows a treatment system employing a laser-driven accelerator to irradiate a patient with a high-energy photon beam, according to one or more embodiments of the disclosed subject matter.

In an alternative configuration, the laser-driven accelerator system can produce high-energy photons (i.e., X-ray photons having energies greater than 10 MeV). Referring to FIG. 1B, an embodiment of such a high-energy photon treatment system 100B is shown. The treatment system 100B can include a laser-driven accelerator system 110B. In the accelerator system 110B, a laser 102 drives an electron accelerator 106 (or other particle accelerator) to generate pulses 122 of radiation, as described above. The pulses 122 can then impact an X-ray generation target (e.g., a tungsten target) to generate pulses of X-ray radiation 138. A collimator system 136, such as a multi-leaf collimator, can be used to shape the X-ray pulses into a narrow beam 144 directed along irradiation axis 123.

The pulsed photon beam 114 can be directed from the accelerator system 110B toward the treatment volume 130 within the patient 126. As discussed above, the treatment volume 130 may be subject to motion within the patient 126, which motion may be on the order of milliseconds or seconds. But since each pulse of the photon beam 144 corresponds to the short pulses of the electron beam 122, the photon beam 144 can be delivered to the patient during a time when the treatment volume can be considered to be substantially stationary (or with negligible change in location) and while the locations of the irradiation axis 123 and the treatment volume 130 coincide.

As with the embodiment of FIG. 1A, the location of the treatment volume 130 can be monitored by the monitoring system 112 during irradiation with the photon beam 144, or at least prior to a dose fraction comprising one or more photon pulses, and irradiation of the patient can be adjusted responsively thereto. The results of the monitoring by system 112 can be communicated to the system controller 118, which can control (i.e., by sending one or more control signals) the accelerator system 110B and/or a moveable support of the accelerator system (not shown) to re-position the photon beam 144 with respect to the changed location of the treatment volume 130. For example, the photon beam 144 can be steered or have its spot size modified (i.e., using collimator system 136) to follow the treatment volume (or portions thereof) despite motion of the treatment volume. Alternatively or additionally, the system controller 118 can control the accelerator system 110B such that the patient 126 is only irradiated when the treatment volume 130 is located along the irradiation axis 123 of the stationary photon beam 144. The control system 118 can also coordinate the timing of imaging by the monitoring system 112, laser pulse generation by laser 102, and/or photon beam irradiation from accelerator system 110B.

The photon beam 144 is unaffected by the magnetic fields generated by monitoring system 112 and/or beam control system 112. However, secondary electrons may be produced by the high energy photon beam primarily due to Compton scattering. Thus, the beam control system 114 can apply a longitudinal magnetic field (i.e., along direction 132 parallel to irradiation axis 123), the magnetic field may reduce the spread of secondary electrons, as described above with respect to FIGS. 2C-2D.

Figure 2E:
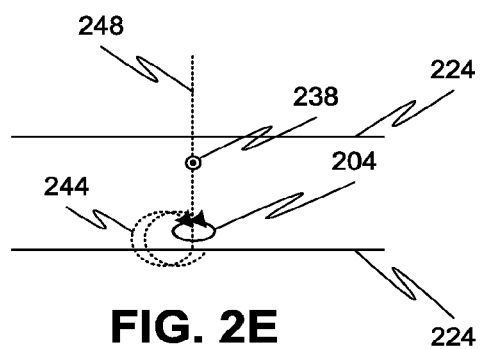
FIG. 2E illustrates the effect on secondary electrons exiting a treatment volume of a transverse magnetic field, according to one or more embodiments of the disclosed subject matter.

Alternatively or additionally, the beam control system 114 can apply a transverse magnetic field (i.e., along direction 238, which is directed out of the page), as illustrated in FIG. 2E. When the secondary electrons leave solid tissue of the patient 224 and reach air, the secondary electrons can be turned back to the treatment volume (as shown by 244) due to the force generated by the transverse magnetic field. The redirected secondary electrons can thus enhance the dose received by the patient.

As with the embodiment of FIG. 1A, the timing of the monitoring, photon beam generation and irradiation, and magnetic field control in the embodiment of FIG. 1B can be controlled according to FIG. 3. However, since the photon beam is not affected by magnetic fields, the monitoring period 302 can overlap the generation 306 and irradiation 308 periods, whether magnetic or non-magnetic medical imaging techniques are used. The magnetic field control period 304 can then be used to control the secondary electrons rather than control the photon beam 144. Alternatively or additionally, the system can employ predictive tracking, using, for example, template matching, as described in the '398 patent incorporated by reference above, or other predictive tracking techniques.

Figure 1C:
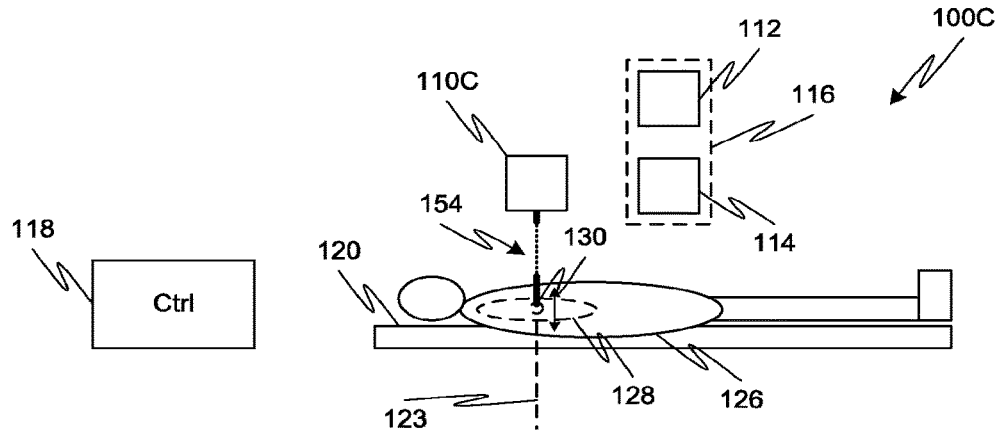
FIG. 1C shows another treatment system employing a laser-driven accelerator to irradiation a patient with a high-energy photon beam, according to one or more embodiments of the disclosed subject matter.

In another alternative configuration, the laser-driven accelerator system can produce high-energy radiation (i.e., either electrons or X-ray photons) and employ a magnetic field transverse to the irradiation axis 123. Referring to FIG. 1C, an embodiment of such a high-energy treatment system 100C is shown. The treatment system 100C can include a laser-driven accelerator system 110C, which generates high energy electrons or high energy photons, as described above with respect to FIGS. 1A-1B. In some embodiments, the accelerator system 110C may be located close to the patient (e.g., less than 1 m from the patient) so that the distance the radiation beam 154 travels to the treatment volume 130 is minimized, or at least reduced.

The pulsed radiation beam 154 can be directed from the accelerator system 110C toward the treatment volume 130 along an irradiation axis 123. As with the embodiments of FIGS. 1A-1B, the location of the treatment volume 130 can be monitored by the monitoring system 112 during irradiation with the beam 154, or at least prior to a dose fraction comprising one or more pulses, and irradiation of the patient can be adjusted responsively thereto. The results of the monitoring by system 112 can be communicated to the system controller 118, which can control (i.e., by sending one or more control signals) the accelerator system 110C and/or a moveable support of the accelerator system (not shown) to re-position the beam 154 with respect to the changed location of the treatment volume 130. Alternatively or additionally, the system controller 118 can control the accelerator system 110C such that the patient 126 is only irradiated when the treatment volume 130 is located along the irradiation axis 123 of the stationary beam 154.

The beam control system 114 can apply a transverse magnetic field (i.e., along direction 152 (coming out of the page) that is perpendicular to the irradiation axis 123). Since the accelerator system 110C is small and can be located close to the body of the patient 126, the impact of the transverse magnetic field on the beam 154 can be minimized. Moreover, when the beam 154 is a photon beam, the transverse magnetic field will have no effect on the beam itself. But the transverse magnetic field can control secondary electrons that result from the beam 154 within the patient 126. As described above with respect to FIG. 2E, when the secondary electrons leave solid tissue of the patient and reach air, the secondary electrons can be turned back to the treatment volume due to the force generated by the transverse magnetic field to enhance the dose received by the patient.

Figure 4A:
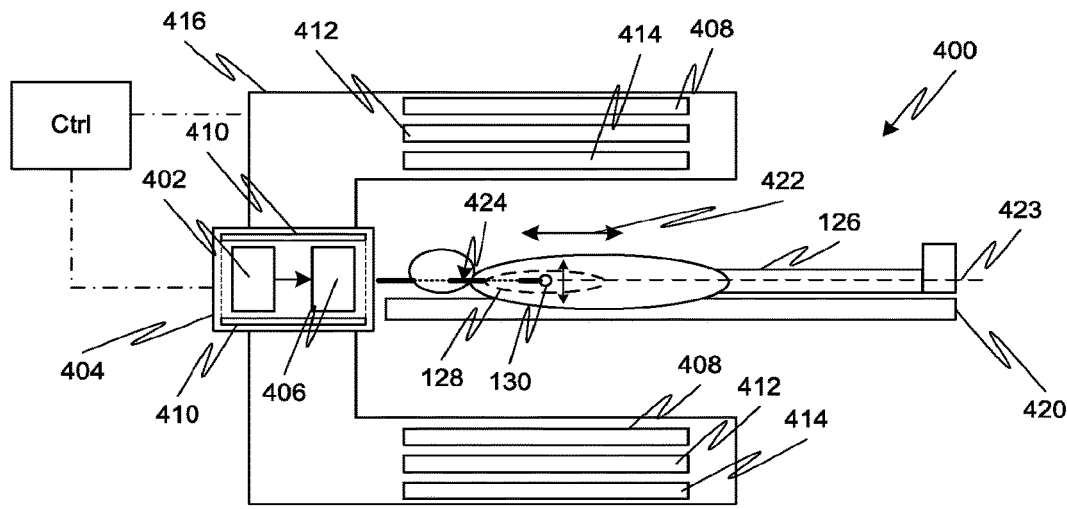
FIG. 4A is a simplified side view of a high-energy electron treatment system employing a laser-driven accelerator and a magnetic resonance imaging (MRI) system generating a longitudinal magnetic field, according to one or more embodiments of the disclosed subject matter.

An embodiment of a treatment system 400 using an MRI system 416 for both monitoring of treatment volume 130 and controlling spread of electron beam 424 is shown in FIG. 4A. The treatment system 400 can include an electron beam generation system 404 with a laser 402 and an acceleration unit 406. Laser pulses from the laser 402 are fed to the acceleration unit 406 to produce electron beam 424, which is subsequently fed to the patient 126 held by support 420 within the MRI system 416. In such a configuration, the acceleration unit 406 may be considered the irradiation head, although a separate irradiation head (not shown) with bend magnets to redirect the electron beam 424 along irradiation axis 423 may optionally be provided. The electron beam generation system 404 can also include a compensation device 410, for example, a compensation coil, which reduces the effect of the magnetic fields of the MRI system 416 on the electrons within electron beam generation system 404.

Although shown mounted at a particular location with respect to the MRI system 416 and the patient 126, it is also contemplated that electron beam generation system 404 may be disposed at other locations (for example, as illustrated in FIGS. 4B-9C). In general, however, because the energies of the electron beam are so high (e.g., 50-250 MeV), it is desirable to have the exit window of the beam generation system 404 to be as close to the treatment surface as practical to minimize, or at least reduce, energy loss, ozone production, and any undesired beam effects prior to entry of the beam into the patient. For example, the exit window may be spaced from the treatment surface of the patient and/or the treatment volume 130 less than 1 m.

The MRI system 416 can include components of a standard MRI machine, for example, one or more magnets 408 that generate a static magnetic field, one or more gradient coils 412, and one or more RF coils 414. The MRI system 416 may surround the patient 126, with the patient treatment volume 130 disposed along a central axis of the MRI system. As with other embodiments, a control system 418 can be provided to coordinate operation of the electron beam generation system 404 and the MRI system 416, for example, to perform monitoring of the treatment volume 130 prior to electron beam 424 generation and to generate an appropriate longitudinal magnetic field (i.e., along direction 422 and parallel to beam irradiation axis 423) to control beam spread of the electron beam 424 during irradiation.

Figure 4B:
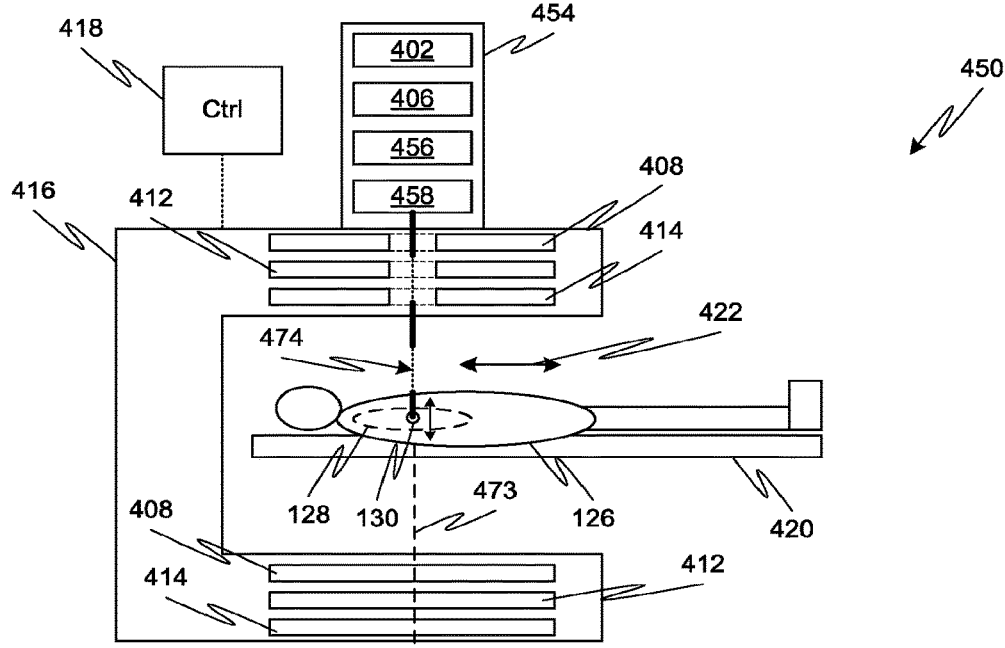
FIG. 4B is a simplified side view of a high-energy photon treatment system employing a laser-driven accelerator and an MRI system generating a transverse magnetic field, according to one or more embodiments of the disclosed subject matter.

An embodiment of a treatment system 450 that uses an MRI system 416 for monitoring treatment volume 130 and controlling secondary electrons is shown in FIG. 4B. The treatment system 450 can include a photon beam generation system 454 with a laser 402, an acceleration unit 406, an X-ray target 456, and a collimator system 458. Laser pulses from the laser 402 are fed to the acceleration unit 406 to produce an electron beam, which is subsequently fed to the target 456 to generate X-rays. The collimator system 458 narrows the generated X-ray to produce high energy photon beam 474 directed along an irradiation axis 473.

Although shown mounted radially outward from the MRI system 416, it is contemplated that photon beam generation system 454 may be disposed radially inward of the MRI system 416. Indeed, other positions and arrangements of the MRI system 416, the patient 126, and the photon beam generation system 454 are also possible according to one or more contemplated embodiments. Indeed, as with the embodiment of FIG. 4A, it may be desirable to position the exit window of the photon beam generation system 454 as close to the treatment surface of the patient as practical to minimize, or at least reduce, energy loss, ozone production, and any undesired beam effects prior to entry of the beam into the patient.

Although a single laser 402 and accelerator 406 are shown in FIGS. 4A-4B, embodiments of the disclosed subject matter are not limited thereto. Rather, variations on the number of lasers and plasma accelerators are also possible according to one or more contemplated embodiments.

Figure 5A:
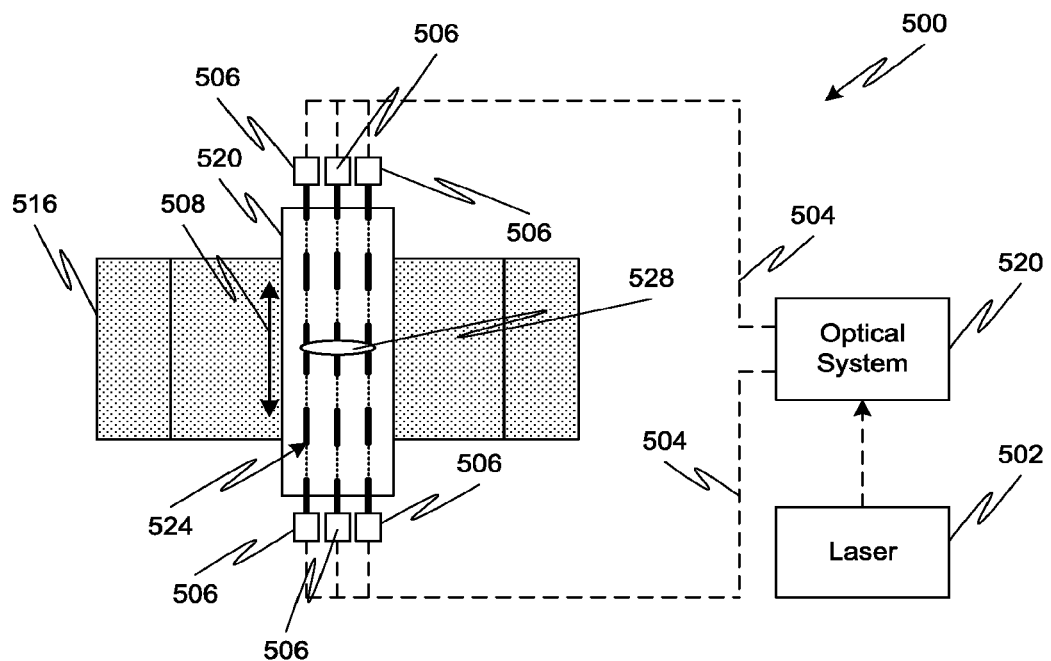
FIG. 5A is a simplified top view of a high-energy electron treatment system employing a single laser driving a plurality of accelerators and an MRI system generating a longitudinal magnetic field, according to one or more embodiments of the disclosed subject matter.

For example, an embodiment of a treatment system 500 employing a single laser 502 and an array of accelerators 506 is shown in FIG. 5A. The patient may be supported at a center of the MRI system 516 by a patient support 520 to receive generated electron beams 524 and magnetic fields from the MRI system 516. Each plasma accelerator 506 can be mounted axially outward from the MRI system 516 and arranged with respective irradiation axes parallel to the magnetic field direction 508 and passing through a desired target location 528. Although shown outward from the MRI system 516, it is also contemplated that accelerators 506 may be disposed within the axial extent of the MRI system 516. In addition, although a one-dimensional array of accelerators 506 is specifically illustrated in FIG. 5A, other configurations are also possible. For example, the accelerators could be arrayed in two dimensions by stacking accelerators on top of each other (i.e., perpendicular to the plane of the page in FIG. 5A).

One or more laser pulses from laser 502 are directed to each accelerator 506 by an optical system 520. The optical system 520 may include, for example, lenses, mirrors, prisms, or any other optical components for processing (e.g., splitting, grating) and directing the laser pulse for use by the accelerators 506. In particular, an optical transport network 504 can convey the laser pulse from optical system 520 to one or more of the accelerators 506 for use in generating the electron beam 524. For example, the optical transport network 504 can include waveguides and/or free space optics.

Although each electron beam 524 from the plurality of accelerators 506 is shown in FIG. 5A, it is also contemplated that the laser pulsing and subsequent electron beam generation can be sequential rather than simultaneous. That is, one of the accelerators 506 may fire an electron beam 524 at a first time, followed by firing of an electron beam 524 by a second accelerator 506 at a later second time, followed by firing of an electron beam 524 by a third accelerator 506 at a still later third time, etc. Pulses from the laser 502 may be directed by optical system 520 via optical transport network 504 to the appropriate accelerator 506 to provide the sequential firing. The pattern of sequential firing may correspond to predicted or monitored motion of the target location 528, for example, such that the generated beams follow the motion of the target location 528.

Alternatively, a first subset of the accelerators 506 may be fired simultaneously, e.g., by splitting a laser pulse of sufficient power among the different accelerators using optical system 520 and optical transport network 504. In still another alternative, all of the plasma accelerators 506 may be fired simultaneously, e.g., by splitting a laser pulse of sufficient power among the different accelerators 506 using optical system 520 and optical transport network 504.

Figure 5B:
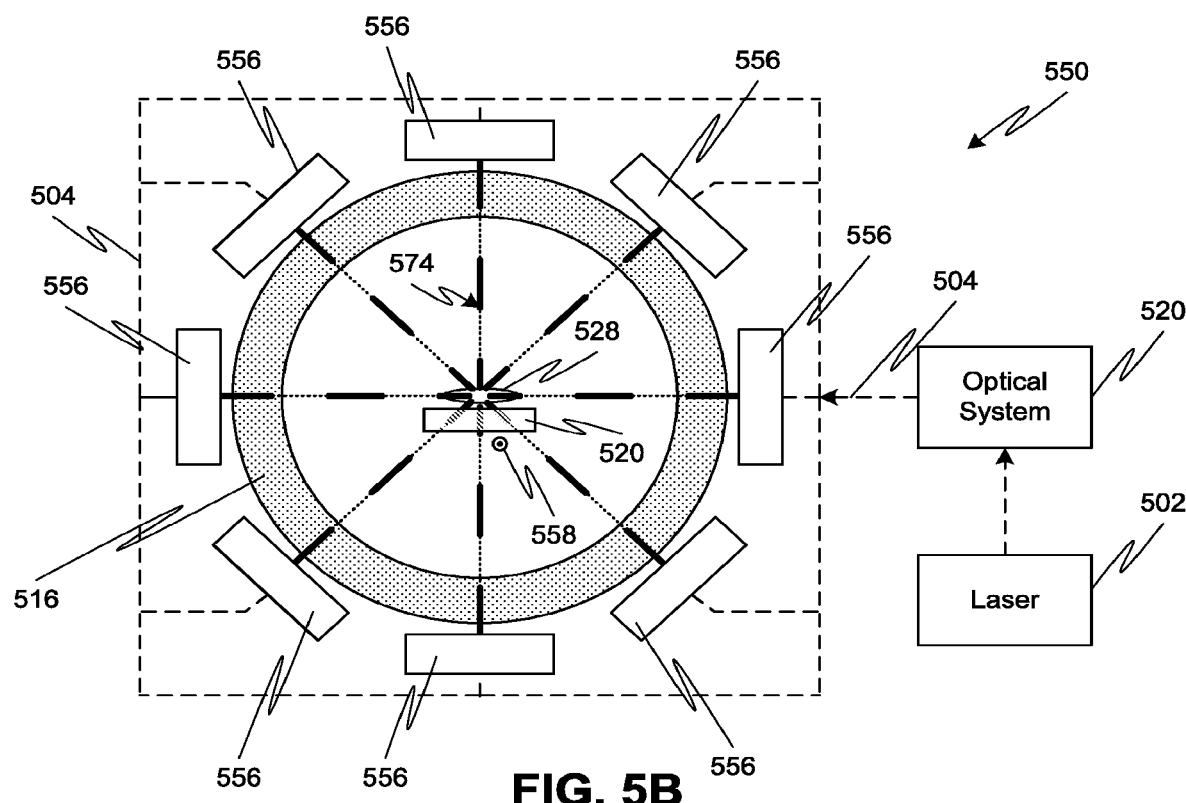
FIG. 5B is a simplified side view of a high-energy photon treatment system employing a single laser driving a plurality of accelerators and an MRI system generating a transverse magnetic field, according to one or more embodiments of the disclosed subject matter.

An embodiment of a treatment system 550 employing a single laser 502 and an array of photon beam generation heads 556 is shown in FIG. 5B. The patient may be supported at a center of the MRI system 516 by a patient support 520 to receive generated electron beams 524 and magnetic fields from the MRI system 516. Each photon beam generation head 556 can include a laser-driven accelerator that produces electrons, an X-ray producing target, and a collimator. Similar to the operation of FIG. 5A, one or more laser pulses from laser 502 can be directed to each beam generation head 556 by an optical system 520 and optical transport network 504 to generate the high-energy photon beams 574, either sequentially or simultaneously.

The photon beam generation heads 556 can be mounted axially outward from the MRI system 516 and arranged with respective irradiation axes perpendicular to the magnetic field direction 558 and passing through a desired target location 528. Although shown disposed radially outward from the MRI system 516, it is also contemplated that photon beam generation heads 556 may be disposed radially inward of the MRI system 516. In addition, although a circular array of photon beam generation heads 556 is specifically illustrated in FIG. 5B, other configurations are also possible. For example, the beam generation heads 556 could be arrayed in two dimensions by stacking the circular arrays on top of each other (i.e., perpendicular to the plane of the page in FIG. 5B).

Figure 6A:
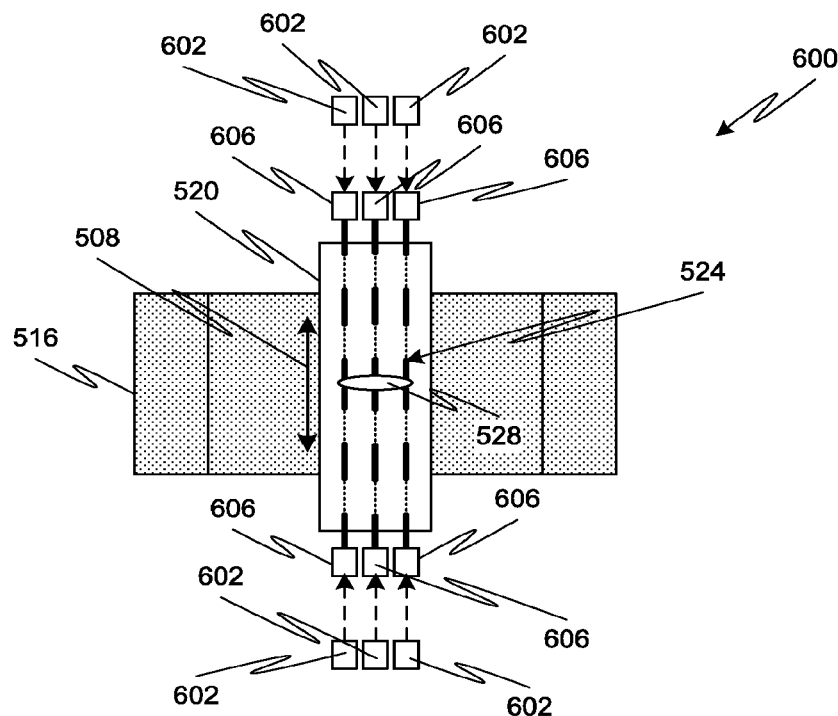
FIG. 6A is a simplified top view of a high-energy electron treatment system employing multiple lasers and accelerators with an MRI system generating a longitudinal magnetic field, according to one or more embodiments of the disclosed subject matter.

In another example, an embodiment of a treatment system 600 employs an array of lasers 602 and a respective array of accelerators 606, as shown in FIG. 6A. The patient may be supported at a center of the MRI system 516 by a patient support 520 to receive generated electron beams 524 and magnetic fields from the MRI system 516. Each accelerator 606 and/or each laser 602 can be mounted axially outward from the MRI system 516 and arranged with respective irradiation axes parallel to the magnetic field direction 508 and passing through a desired target location 528. Although shown mounted outward from the MRI system 516, it is also contemplated that accelerators 606 may be disposed within the axial extent of the MRI system 516. In addition, although a one-dimensional array of lasers 602 and accelerators 606 is specifically illustrated in FIG. 6A, other configurations are also possible. For example, the lasers 602 and accelerators 606 could be arrayed in two dimensions by stacking lasers and accelerators on top of each other (i.e., perpendicular to the plane of the page in FIG. 6A).

Laser pulses from each laser 602 are directed to a respective accelerator 606, for example, through free space or via an optical transport network (not shown), to generate respective electron beams 524. Although each electron beam 524 from the plurality of accelerators 606 is shown in FIG. 6A, it is also contemplated that the laser pulsing and subsequent electron beam generation can be sequential rather than simultaneous. That is, one of the accelerators 606 may fire an electron beam 524 at a first time, followed by firing of an electron beam 524 by a second accelerator 606 at a later second time, followed by firing of an electron beam 524 by a third accelerator 606 at a still later third time, etc. Firing of each laser 602 may be coordinated to provide the sequential electron beam firing, for example, to follow detected or predicted movement of a target volume 528. Alternatively, a first subset of the accelerators 606 may be fired simultaneously, e.g., by coordinated firing of respective lasers 602. In still another alternative, all of the accelerators 606 may be fired simultaneously, e.g., by coordinated firing of all lasers 602.

As noted above, the laser and/or the electron accelerator (e.g., the electron beam generation system) can be mounted on a positioning system that moves the generated electron beam with respect to a treatment volume in the patient. The positioning system may be disposed outward from the MRI system (e.g., farther from the patient than the MRI system) or inward of the MRI system (e.g., closer to the patient than the MRI system). In some embodiments, the MRI system and the positioning system for the electron beam generation system can be integrated into a single system.

Figure 6B:
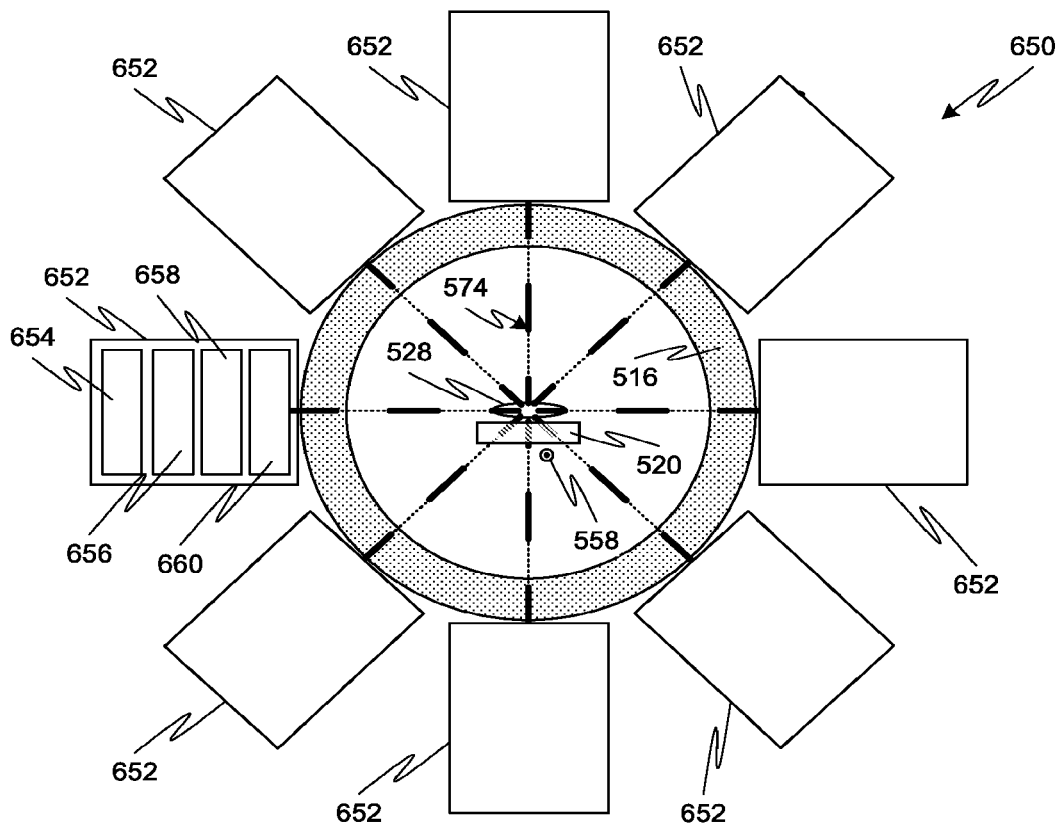
FIG. 6B is a simplified side view of a high-energy photon treatment system employing multiple lasers and accelerators with an MRI system generating a transverse magnetic field, according to one or more embodiments of the disclosed subject matter.

In still another example, an embodiment of a treatment system 650 employs an array of photon beam generation heads 652, as shown in FIG. 6B. The patient may be supported at a center of the MRI system 516 by a patient support 520 to receive generated photon beams 574 and magnetic fields (parallel to direction 558 coming out of the page) from the MRI system 516. Each photon beam generation head 652 can include a laser 654 that drives an accelerator 656 to produce electrons incident on a target 658 to produce X-ray photons. A collimator 660 in each photon beam generation head 652 narrows generated X-rays into a photon beam 574. Note that in FIG. 6B, only one photon beam generation head 652 is illustrated with the laser 654, accelerator 656, target 658, and collimator 660 for the sake of clarity, although each generation head 652 would similarly include the same components.

Figure 7:
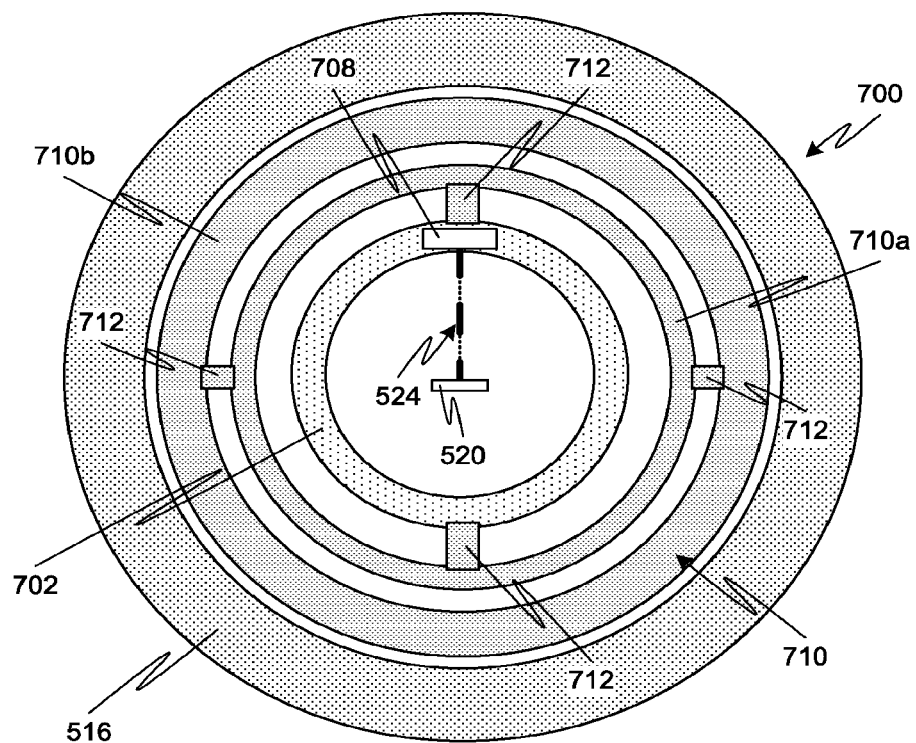
FIG. 7 is a simplified side view of a high-energy treatment system with a laser-driven accelerator mounted on a double-gimbaled O-ring, according to one or more embodiments of the disclosed subject matter.

The photon beam generation heads 652 can be mounted axially outward from the MRI system 516 and arranged with respective irradiation axes perpendicular to the magnetic field direction 558 and passing through a desired target location 528. Although shown disposed radially outward from the MRI system 516, it is also contemplated that photon beam generation heads 652 may be disposed radially inward of the MRI system 516. In addition, although a circular array of photon beam generation heads 652 is specifically illustrated in FIG. 6B, other configurations are also possible. For example, the beam generation heads 652 could be arrayed in two dimensions by stacking the circular arrays on top of each other (i.e., perpendicular to the plane of the page in FIG. 6B). In another example, a treatment system 700 employs a positioning and support system for an irradiation head 708 of the electron beam generation system, as shown in FIG. 7. The positioning and support system can be separate from the MRI system 516, which may be disposed radially outward (or radially inward) from the positioning system. For example, the positioning system can include a support ring 702 and a double-gimbaled O-ring 710, with an inner gimbal ring 710a capable of rotating about a first axis and an outer gimbal ring 710b capable of rotating about a second axis orthogonal to the first axis. A control system (not shown) can coordinate rotation about joints 712 of each gimbal ring 710a, 710b, for example, by controlling respective motors (not shown) mounted on rings 710a, 710b or at joints 712. In an alternative, one or more of support ring 702 and O-rings 710a, 710b can be omitted. For example, only one of the O-rings 710a, 710b may be used with the support ring 702 to hold and position the irradiation head 708 of the electron beam generation system.

Figure 8:
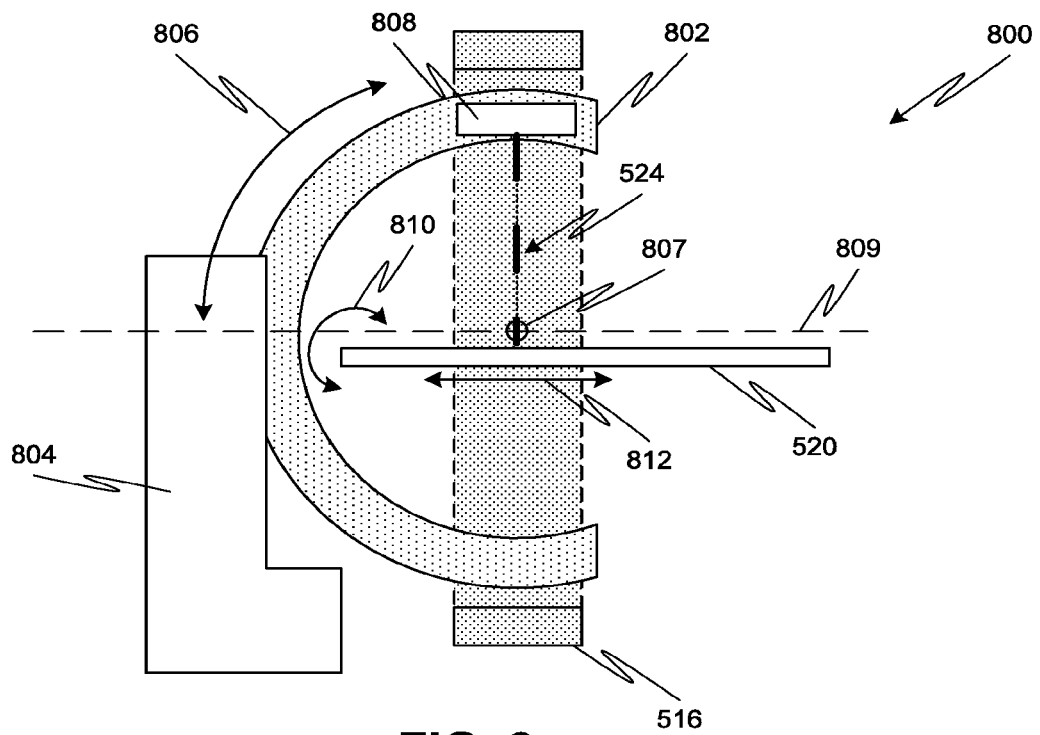
FIG. 8 is a simplified side view of a high-energy treatment system with a laser-driven accelerator mounted on a C-ring gantry, according to one or more embodiments of the disclosed subject matter.

In another example, a treatment system 800 can employ a positioning and support system for an irradiation head 808 of the electron beam generation system, as shown in FIG. 8. The positioning and support system can be separate from the MRI system 516, which may be disposed radially outward (or radially inward) from the positioning system. For example, the positioning system can include a C-arm 802 and a support base 804 coupled thereto. A control system (not shown) can coordinate movements of the C-arm 802, for example, by controlling respective motors (not shown) in the support base 804 to rotate and/or more the C-arm with respect to one or more axes. For example, the C-arm 802 may be rotated along its perimeter about a center 807, i.e., in a direction 806. Alternatively or additionally, the C-arm 802 may be rotated about an axis 809, i.e., in a direction 810.

Figure 9A:
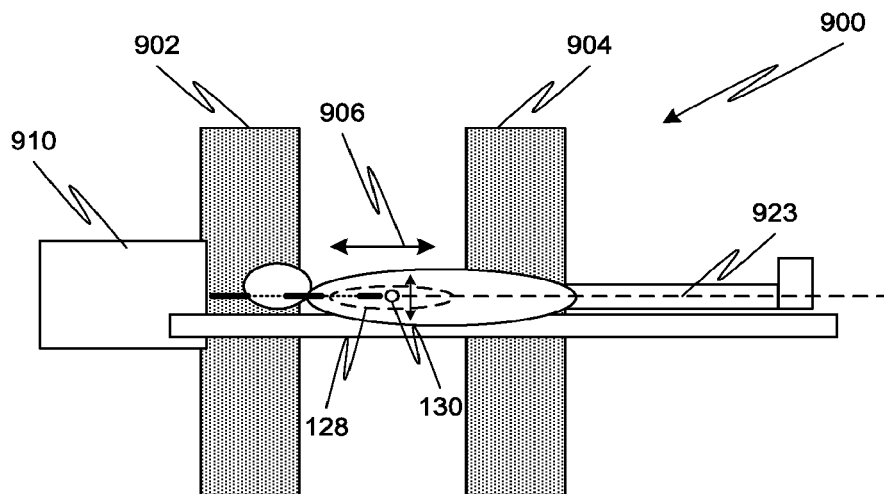
FIG. 9A is a simplified transverse side view of a high-energy treatment system with a laser-driven accelerator and a split-pole MRI generating a longitudinal magnetic field, according to one or more embodiments of the disclosed subject matter.
Figure 9B:
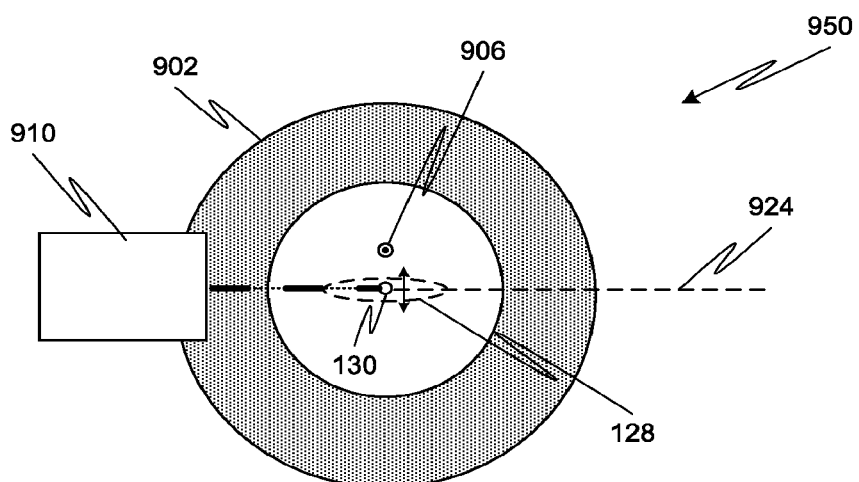
FIG. 9B is a simplified axial side view of a high-energy treatment system with a laser-driven accelerator and a split-pole MRI generating a transverse longitudinal magnetic field, according to one or more embodiments of the disclosed subject matter.
Figure 9C:
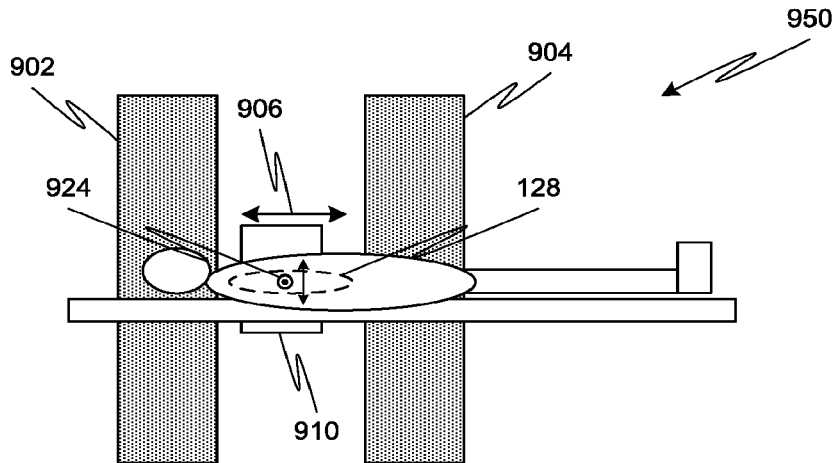
FIG. 9C is a simplified transverse side view of the high-energy treatment system of FIG. 9B.

Although embodiments and descriptions have been provided above with respect to a particular configuration of MRI system, other configurations for the MRI system are also possible according to one or more contemplated embodiments. For example, a split pole MRI setup could be employed as illustrated in FIGS. 9A-9C. The MRI thus includes a first pole 902 and a second pole 904 that together generate a magnetic field in a direction parallel to 906 near the treatment volume 130. A laser-driven beam generation system 910 (e.g., generating high energy electrons or high energy photons) can be oriented with an irradiation axis 923 parallel to the magnetic field direction 906, as in setup 900 of FIG. 9A, or with irradiation axis 924 perpendicular to the magnetic field direction 906, as in setup 950 of FIGS. 9B-9C. Operation of the setups 900, 950 may be similar to the other embodiments described above. It is noted that with respect to any of FIGS. 4A-9C, where specific reference has been made to producing an electron beam or a photon beam, the specific reference does not exclude the use of the other type of beam (and associated components to produce and/or control said beam) in the illustrated configuration. Thus, FIGS. 4A, 5A, and 6A could employ photon beams (and their associated components) rather than electron beams, and FIGS. 4B, 5B, and 6B could employ electron beams (and their associated components) rather than photon beams. Unless otherwise explicitly specified herein, the embodiments discussed as using electron beams can be replaced with photon beams, and vice versa.

It is further noted that although specific embodiments have been discussed above with respect to a combined imaging and magnetic field generation system, embodiments of the disclosed subject matter are not limited thereto. Rather, the functions of imaging and magnetic field generation can be separated, for example, by using an MRI to provide imaging of the treatment volume and a separate solenoid to provide magnetic field generation. Nor are embodiments of the disclosed subject mattering limited to using an MRI for imaging. Rather, non-magnetic medical imaging modalities, such as X-ray imaging, nuclear imaging, ultrasound imaging, optical imaging, and infrared imaging, may also be employed to certain advantage. For example, the use of non-magnetic medical imaging modalities allows for decoupling between the imaging and magnetic field control of electrons (either primary or secondary), such that both may occur simultaneously without negatively affecting each other.

Figure 10:
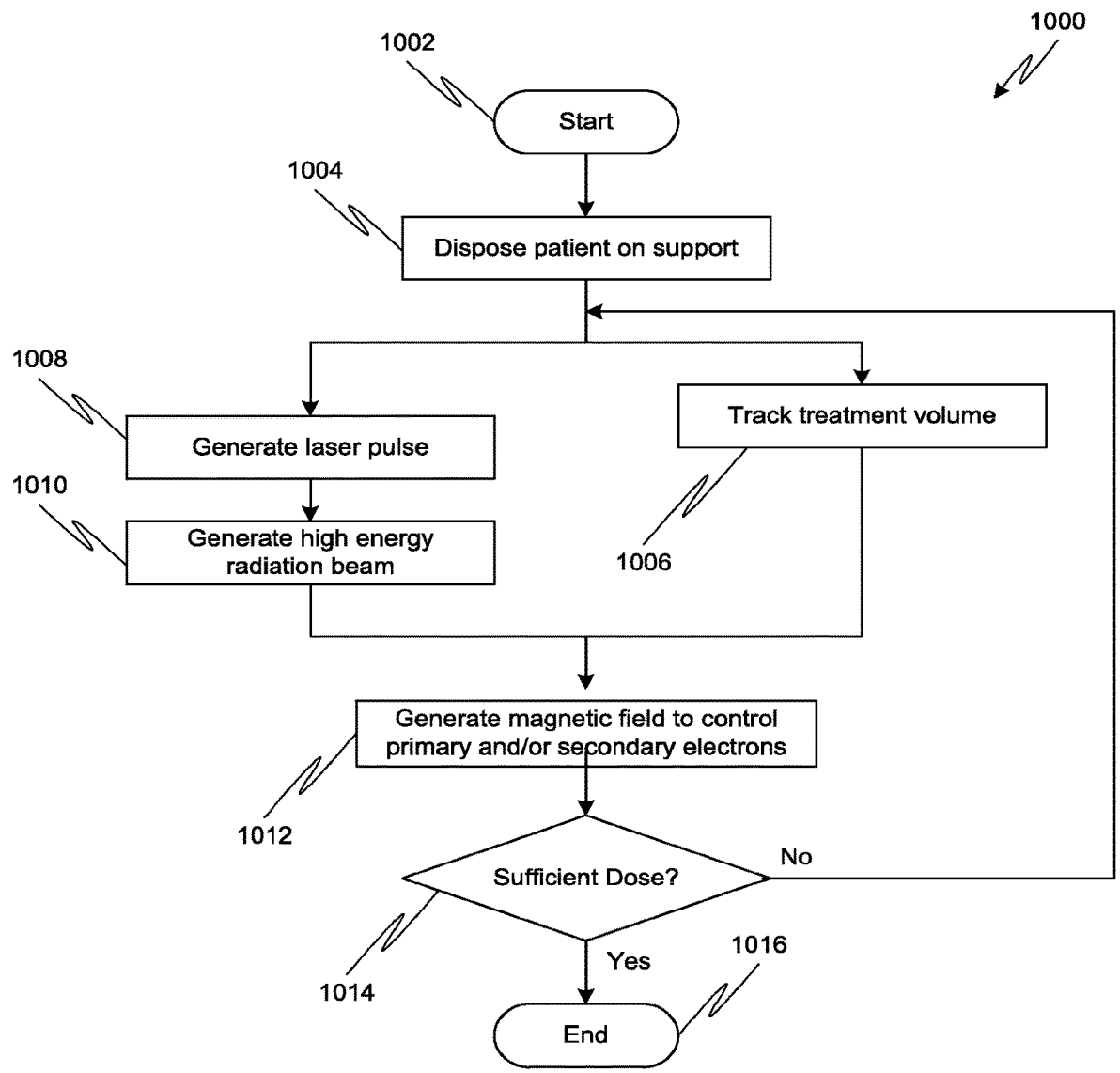
FIG. 10 is a process flow diagram illustrating aspects of a treatment method employing high-energy electrons, according to one or more embodiments of the disclosed subject matter.

In one or more embodiments, methods for treating a patient with high-energy electrons employ any of the disclosed systems or combinations thereof. For example, FIG. 10 illustrates a process flow for a method 1000 for treating a patient with high-energy radiation. The treatment method 1000 can begin at 1002 and proceed to 1004, where a patient is prepared for the treatment. In particular, the patient can be disposed on a patient support, which is used to hold the patient with respect to the treatment system that can both image and irradiate the patient in a single treatment session (i.e., without having to move the patient or the patient support to a different machine).

With the patient disposed on the patient support, the method can proceed to 1006, where a location and/or movement of a particular treatment volume (e.g., a tumor within the lung, thorax, head, or neck of the patient) can be tracked. For example, the treatment volume may be one that tends to move over time, either due to motion of the patient or due to motion of an organ within the patient (e.g., due to breathing by the patient). The tracking by the treatment system may monitor the location and/or movement of the treatment volume at any particular time in order to adjust irradiation to compensate for any changes in its location. For example, the irradiation may be controlled such that the patient is only irradiated when the treatment volume is aligned with a static irradiation axis of the radiation beam. The tracking may comprise imaging of the patient and/or the treatment volume therein and image processing of the images to track the location and/or movement of the treatment volume. For example, the tracking may be performed by an MRI machine. Alternatively or additionally, the tracking may comprise predictive tracking, using, for example, template matching, as described in the '398 patent incorporated by reference above, or other predictive tracking techniques.

After or contemporaneously with the tracking at 1006, the method at 1008 can generate one or more pulses from a laser. Each resulting laser pulse is directed to an accelerator system, for example, a plasma accelerator or a dielectric microstructure, where a corresponding pulse of high-energy electrons is generated at 1010. The electrons can further serve to generate X-rays for subsequent patient irradiation or can be sent to the patient for direct irradiation. Each pulse of high-energy electrons can be less than 100 fs, for example, in a range of 20 fs-100 fs, and have a charge rate on the order of 1 nC/pulse. Moreover, the accelerated electrons can have an energy of at least 50 MeV, for example, in a range of 50-300 MeV.

Since the electrons may be affected by magnetic fields generated during the tracking 1006, the electron acceleration 1010 may occur after the tracking 1006. Alternatively or additionally, a compensation device (e.g., cancellation coil) can be used to shield generated electrons from a magnetic field, thereby allowing the acceleration 1010 to occur simultaneously with (or at least partially overlapping with) the tracking 1006.

At 1010, the accelerated electrons can form a pulsed electron beam (e.g., where one or more pulses comprises an individual dose fraction) that is directed to the patient on the patient support for irradiation by an appropriate positioning system. As the electron beam travels to the patient, the electron beam can be focused at 1012. A longitudinal magnetic field can be applied to focus the electron beam, i.e., to limit a transverse spread of the electron beam as it travels from the irradiation head to the treatment volume in the patient. For example, the magnetic field can be applied by the same MRI machine that performs the imaging. Thus, the focusing 1012 can occur subsequent to the tracking 1006. Alternatively or additionally, the magnetic field can be applied by a separate system, e.g., employing a solenoid. The magnetic field may be sufficient to limit the transverse growth of the electron beam comprising the generated electrons, so as to have a beam spot size less than a size of the treatment volume, for example, less than 200 μm. The magnetic field to focus the pulsed electron beam can have a field strength of at least 1 T, for example, in a range from 1-10 T, in a range from 3-6 T, or greater than 6 T.

Additionally or alternatively, at 1010, the accelerated electrons can generate high-energy photons (e.g., X-rays have energies greater than 10 MeV), which are collimated to from a photon beam directed to the patient on the patient support for irradiation. As the photon beam travels within the patient, it generates secondary electrons primarily via the Compton Effect, which secondary electrons can be focused at 1012 by a longitudinal magnetic field. For example, the magnetic field can be applied by the same MRI machine that performs the imaging. Thus, the magnetic field control 1012 can occur subsequent to the tracking 1006. Alternatively or additionally, the magnetic field can be applied by a separate system, e.g., employing a solenoid.

Additionally or alternatively, at 1012, a transverse magnetic field can be applied to control secondary electrons that are generated by either a high-energy primary electron beam or a high-energy photon beam and that propagate from the patient into the air. For example, the magnetic field can be applied by the same MRI machine that performs the imaging. Thus, the magnetic field control 1012 can occur subsequent to the tracking 1006. Alternatively or additionally, the magnetic field can be applied by a separate system, e.g., employing a solenoid. The timing between the tracking 1006 and the magnetic field control 1012 may be such that there is minimal opportunity for the treatment volume to move. For example, the timing may be less than 1 ms, e.g., on the order of the pulse length of the electron beam (e.g., 20-100 fs). The resulting pulsed radiation beam can have a spot size (either immediately after the exit window of the acceleration system or at the treatment volume) less than 200 μm, for example, in a range of 20 μm-200 μm and can provide a dose rate to the treatment volume of at least 0.5 Gy/s, for example, in a range of 0.5-50 Gy/s.

After each dose fraction of radiation (each dose fraction comprising a single pulse or a series of successive pulses on a sufficiently short time scale (i.e., less than 1 ms)), it can be determined at 1014 whether a sufficient total dose has been received by the treatment volume. Since any generated secondary electrons could increase the dose received by the patient, these secondary electrons, as well as the effects of any longitudinal and/or transverse magnetic fields on the secondary electrons and the radiation beam, should be taken into account in determining whether a sufficient dose has been received at the treatment volume. For example, treatment planning algorithms can be used to take into account the above factors. Measurements can be made prior to patient treatment using water tanks or other dosimetric phantoms. Radiation transport codes (e.g., Monte Carlo simulations) that model the physics in the patient can be used and compared to phantom data. The treatment planning algorithm can take into account simulation and phantom data to make accurate calculations on dose distribution and whether a sufficient dose has been delivered to the patient.

If a sufficient dose has not been received, the method can return to the tracking 1006 and the generating 1008 for subsequent irradiation of the patient, where the position of the radiation beam can be changed to account for any movement or changes in location of the treatment volume since the last tracking 1006, or the irradiation can be delayed until the treatment volume is again at an appropriate location for irradiation. The tracking 1006, generating laser pulses 1008, generating the radiation beam 1010, and magnetic field control 1012 can be repeated until a sufficient total dose is received, for example, at a repetition rate of approximately 10 Hz. Each tracking 1006 may occur between successive dose fractions of high-energy radiation. If a sufficient dose has been received, the method can proceed to 1016 where the process may terminate.

Although embodiments herein have been described with respect to delivering a radiation beam as treatment for a human patient, embodiments of the disclosed subject matter are not limited thereto. Rather, embodiments can include delivering a radiation beam for irradiating any object or animal. Indeed, where the word "patient" has been used in the specification and claims, such recitations are intended to cover any object or animal as well as humans.

Although embodiments herein have been described with respect to electron beams and X-ray photon beams, the teachings of the present disclosure are not limited thereto. Indeed, as used herein, radiation beam includes any particle or photon beam of sufficient energy to effect medical treatment. For example, proton beams could be used instead of electron beams, with appropriate configuration of the magnetic field, according to one or more contemplated embodiments.

As used herein, "longitudinal" and "transverse" are relative terms used to indicate the general relationship between the direction of beam propagation and the magnetic field lines at regions near the treatment volume. Indeed, it is recognized that the magnetic field lines generated by an MRI (or by some other solenoid configuration) will not be completely parallel, especially near ends of the MRI. Accordingly, the recitations of "longitudinal", "transverse", "parallel", and/or "perpendicular" are intended to include deviations from the ideal (i.e., within 10%). Thus, a longitudinal magnetic field would include a magnetic field that is within 10° of being parallel to the beam propagation axis as measured at a point less than 1 meter from the treatment volume. Similarly, a transverse magnetic field would include a magnetic field that is within 10° of being perpendicular to the beam propagation axis as measured at a point less than 1 meter from the treatment volume.

Moreover, any recitation herein of positions being "coincident", "aligned", "substantially coincident", "substantially aligned", etc. are intended to include variations up to 10%. In general, whenever "substantially", "approximately", or similar language is used herein, variations up to and including 10% are intended.

In one or more first embodiments, a treatment system comprises a laser-drive accelerator system, a patient monitoring system, and a control system. The laser-driven accelerator system can be constructed to irradiate a patient disposed on a patient support. The patient monitoring system can be configured to detect and track a treatment volume within the patient. The control system can be configured to control the laser-driven accelerator system responsively to a location or movement of the treatment volume tracked by the patient monitoring system.

In the first embodiments or any other embodiment, the laser-driven accelerator is a laser-driven plasma accelerator or a laser-driven dielectric microstructure accelerator.

In the first embodiments or any other embodiment, the laser-driven accelerator system generates electrons having energies of at least 50 MeV.

In the first embodiments or any other embodiment, the laser-drive accelerator system generates X-ray photons having energies of at least 10 MeV.

In the first embodiments or any other embodiment, the treatment volume changes position over time, and the control system sends one or more respective control signals to command the laser-driven accelerator system to irradiate the treatment volume at each of the changed positions.

In the first embodiments or any other embodiment, the treatment volume changes positions over time, and the control system sends one or more respective control signals to command the laser-driven accelerator system to irradiate only when the treatment volume position coincides with an irradiation axis of the laser-driven accelerator system.

In the first embodiments or any other embodiment, a focal spot size of an electron beam from the laser-driven accelerator system is less than 200 μm.

In the first embodiments or any other embodiment, the laser-driven accelerator system irradiates the patient with a pulsed electron beam, each pulse being less than 100 fs.

In the first embodiments or any other embodiment, the laser-driven accelerator system produces a dose rate at the treatment volume of at least 0.5 Gy/s.

In the first embodiments or any other embodiment, the patient monitoring system is configured to track the treatment volume in between pulses of the irradiation from the laser-driven accelerator system.

In the first embodiments or any other embodiment, the treatment system comprises a beam control system, which generates a longitudinal magnetic field that is parallel to an irradiation axis of the laser-driven accelerator system. In the first embodiments or any other embodiment, the control system is configured to control the laser-driven accelerator system and/or the beam control system to steer the irradiation axis or to modify a spot size of radiation from the laser-driven accelerator system. In the first embodiments or any other embodiment, the beam control system and the patient monitoring system are the same system and comprise a magnetic resonance imaging system.

In the first embodiments or any other embodiment, the magnetic resonance imaging system is configured to generate a magnetic field having a field strength of at least 1 T.

In the first embodiments or any other embodiment, the laser-driven accelerator system comprises a compensation device that reduces an effect of a generated magnetic field from the beam control system on the electron beam external to the patient. In the first embodiments or any other embodiment, the compensation device comprises cancellation coils.

In the first embodiments or any other embodiment, the beam control system and the patient monitoring system are separate systems. In the first embodiments or any other embodiment, the patient monitoring system comprises at least one of an X-ray imaging system, a nuclear imaging system, an ultrasound imaging system, an optical imaging system, and an infrared imaging system.

In the first embodiments or any other embodiment, the treatment system further comprises at least one additional laser-driven accelerator system that irradiates the patient disposed on the patient support. In the first embodiments or any other embodiment, each laser-driven accelerator system has a laser that feeds a respective accelerator head that directs a respective radiation beam to the patient.

In the first embodiments or any other embodiment, the treatment system further comprises at least one additional laser-driven accelerator system and a laser transport system. The at least one additional laser-driven accelerator system irradiates the patient disposed on the patient support. The laser transport system conveys one or more laser beams to an accelerator chamber of one of the laser-driven accelerator systems.

In the first embodiments or any other embodiment, the treatment system further comprises a positioning system that supports at least an irradiation head of the laser-driven accelerator system thereon. The positioning system can be configured to move the irradiation head with respect to the treatment volume in the patient.

In one or more second embodiments, a treatment method comprises generating a radiation beam using a laser-driven accelerator system. The treatment method can further comprise detecting and tracking a location and/or movement of a treatment volume within a patient disposed on a patient support. The treatment method can also comprise irradiating the patient with pulses of the radiation beam responsively to the tracked location and/or movement of the treatment volume.

In the second embodiments or any other embodiment, the laser-driven accelerator is a laser-driven plasma accelerator or a laser-drive dielectric microstructure accelerator.

In the second embodiments or any other embodiment, the generating a radiation beam comprises generating electrons having energies of at least 50 MeV.

In the second embodiments or any other embodiment, the generating a radiation beam comprises generating X-ray photons having energies of at least 10 MeV.

In the second embodiments or any other embodiment, the tracking occurs between successive pulses of the radiation beam.

In the second embodiments or any other embodiment, the treatment volume comprises a tumor within a lung, thorax, head, or neck of the patient that changes position over time, and the irradiating is such that the treatment volume is irradiated in each changed position.

In the second embodiments or any other embodiment, the treatment volume comprises a tumor within a lung, thorax, head, or neck of the patient that changes position over time, and the irradiating is such that the patient is irradiated only when the treatment volume position coincides with an axis of the radiation beam.

In the second embodiments or any other embodiment, the radiation beam comprises an electron beam, and a focal spot size of the electron beam is less than 200 µm.

In the second embodiments or any other embodiment, the radiation beam comprises an electron beam, and each pulse is less than 100 fs.

In the second embodiments or any other embodiment, the irradiating produces a dose rate at the treatment volume of at least 0.5 Gy/s.

In the second embodiments or any other embodiment, the generating, tracking, and irradiating are performed during a same treatment session of the patient.

In the second embodiments or any other embodiment, the irradiating the patient comprises using a longitudinal magnetic field from a beam control system, and the magnetic field is parallel to an irradiation axis of the laser-driven accelerator system.

In the second embodiments or any other embodiment, the beam control system comprises a magnetic resonance imaging system, and the detecting and tracking comprises forming a magnetic resonance image using said magnetic resonance imaging system.

In the second embodiments or any other embodiment, the magnetic resonance imaging system is configured to generate a magnetic field having a field strength of at least 1 T.

In the second embodiments or any other embodiment, the detecting and tracking comprises forming an image using at least one of an X-ray imaging system, a nuclear imaging system, an ultrasound imaging system, an optical imaging system, and an infrared imaging system.

In the second embodiments or any other embodiment, the treatment method further comprises steering the radiation beam and/or modifying a spot size of the radiation beam between different pulses.

In the second embodiments or any other embodiment, the treatment method further comprises using a compensation device to reduce an effect of a generated magnetic field on the radiation beam from the laser-driven accelerator system.

In the second embodiments or any other embodiment, the treatment method further comprises positioning an irradiation head of the laser-driven accelerator system prior to the irradiated doses of generated electrons using a C-arm or double-gimbaled O-ring positioning system.

In one or more third embodiments, a non-transitory computer-readable storage medium and a computer processing system are provided. A sequence of programmed instructions for controlling a treatment system to irradiate a patient is embodied upon the non-transitory computer-readable storage medium. The computer processing system executes the sequence of programmed instructions embodied on the computer-readable storage medium to cause the computer processing system to track a location and/or movement of a treatment volume within a patient disposed on a patient support and send one or more control signals to a laser-driven accelerator system to generate a radiation beam that irradiates the patient responsively to the tracked location and/or movement of the treatment volume.

In the third embodiments or any other embodiment, the computer-readable storage medium causes the computer processing system to track the location and/or movement of the treatment volume between successive doses from the generated radiation beam.

In the third embodiments or any other embodiment, the treatment volume changes position over time and the computer-readable storage medium further causes the computer processing system to send one or more controls signals to the laser-driven accelerator system such that the treatment volume is irradiated by the generated radiation beam in each changed position.

In the third embodiments or any other embodiment, the treatment volume changes position over time and the computer-readable storage medium further causes the computer processing system to send one or more controls signals to the laser-driven accelerator system such that the patient is irradiated by the generated radiation beam only when the treatment volume position coincides with an axis of the radiation beam.

In the third embodiments or any other embodiment, the computer-readable storage medium further causes the computer processing system to send one or more control signals to a beam control system to generate a longitudinal magnetic field that is parallel to an axis of the generated radiation beam.

In the third embodiments or any other embodiment, the computer-readable storage medium further causes the computer processing system to control an imaging system to generate a magnetic field to image the treatment volume.

In the third embodiments or any other embodiment, the computer-readable storage medium further causes the computer processing system to control at least one of an X-ray imaging system, a nuclear imaging system, an ultrasound imaging system, an optical imaging system, and an infrared imaging system to image the treatment volume and/or the patient.

In the third embodiments or any other embodiment, the computer-readable storage medium further causes the computer processing system to send a signal to control a C-arm or double-gimbaled O-ring positioning system to move an irradiation head of the laser-driven accelerator system. It will be appreciated that the modules, processes, systems, and devices described above can be implemented in hardware, hardware programmed by software, software instruction stored on a non-transitory computer readable medium or a combination of the above. For example, a method for controlling an irradiation system to perform high-energy irradiation can be implemented, for example, using a processor configured to execute a sequence of programmed instructions stored on a non-transitory computer readable medium. For example, the processor can include, but is not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and devices can be implemented as a single processor or as a distributed processor. Further, it should be appreciated that the steps mentioned herein may be performed on a single or distributed processor (single and/or multi-core). Also, the processes, modules, and sub-modules described in the various figures of and for embodiments herein may be distributed across multiple computers or systems or may be co-located in a single processor or system. Exemplary structural embodiment alternatives suitable for implementing the modules, sections, systems, means, or processes described herein are provided below.

The modules, processes, systems, and devices described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example. Embodiments of the methods, processes, modules, devices, and systems (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the methods, systems, or computer program products (software program stored on a non-transitory computer readable medium).

Furthermore, embodiments of the disclosed methods, processes, modules, devices, systems, and computer program product may be readily implemented, fully or partially, in software using, for example, object or object-oriented software development environments that provide portable source code that can be used on a variety of computer platforms. Alternatively, embodiments of the disclosed methods, processes, modules, devices, systems, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the methods, processes, modules, devices, systems, and computer program product can be implemented in hardware and/or software using any known or later developed systems or structures, devices and/or software by those of ordinary skill in the applicable art from the function description provided herein and with a general basic knowledge of particle beam irradiation systems, control systems, and/or computer programming arts.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, systems, devices, and methods for high-energy irradiation. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicant intends to embrace all such alternatives, modifications, equivalents, and variations that are within the spirit and scope of the present invention.

The invention claimed is:

1. A treatment system comprising:
   a laser-driven accelerator system configured to:
      generate a radiation beam; and
      irradiate, along an irradiation axis, a treatment volume within a subject disposed on a support system with the radiation beam, the irradiation causing generation of secondary electrons within the subject;
   a magnetic field control system configured to:
      apply magnetic fields to the radiation beam;
      control a direction of the secondary electrons that exit the subject using the magnetic fields; and
      direct the secondary electrons that exit the subject back into the treatment volume using the magnetic fields;
   a radiation dose determining system configured to determine a total radiation dose received by the treatment volume, the total radiation dose including radiation dose generated by the redirected secondary electrons; and
   a control system configured to adjust the irradiation axis and/or a spot size of the radiation beam from the laser-driven accelerator system based on the determined total radiation dose.

2. The treatment system of claim 1, further comprising a monitoring system configured to track the treatment volume.

3. The treatment system of claim 2, wherein the control system is further configured to control the laser-driven accelerator system responsively to a location or movement of the treatment volume tracked by the monitoring system.

4. The treatment system of claim 3, wherein the control system is further configured to control and coordinate timing of the application of the magnetic fields.

5. The treatment system of claim 4, wherein the control system is further configured to control and coordinate timing of the radiation beam generation, the irradiation of the subject, the tracking of the treatment volume, and the total radiation dose determination.

6. The treatment system of claim 5, wherein the generating of the radiation beam, the tracking of the treatment volume, and the timing of the magnetic field control is repeated until the measured radiation dose achieves a predetermined value.

7. The treatment system of claim 6, wherein the repetition rate is about 10 Hz.

8. The treatment system of claim 6, wherein the timing between the tracking and the magnetic filed control is less than 1 ms.

9. A treatment method, comprising:
   generating a radiation beam using a laser-driven accelerator system;
   irradiating, along an irradiation axis, a treatment volume within a subject disposed on a support system with the radiation beam, the irradiation causing generation of secondary electrons within the subject;

applying magnetic fields to the radiation beam;

controlling a direction of the secondary electrons that exit the subject using the magnetic fields;

directing the secondary electrons that exit the subject back into the treatment volume using the magnetic fields;

determining a total radiation dose received by the treatment volume, the total radiation dose including radiation dose generated by the redirected secondary electrons; and adjusting the irradiation axis and/or a spot size of the radiation beam based on the determined total radiation dose.

10. The treatment method of claim 9, further comprising tracking the treatment volume.

11. The treatment method of claim 10, further comprising controlling the laser-driven accelerator system responsively to a location or movement of the tracked treatment volume.

12. The treatment method of claim 11, further comprising controlling and coordinating timing of the application of the magnetic fields.

13. The treatment method of claim 12, further comprising controlling coordinating timing of the radiation beam generation, the irradiation of the subject, the tracking of the treatment volume, and the total radiation dose determination.

14. The treatment method of claim 13, further comprising repeating the generating of the radiation beam, the tracking of the treatment volume, and the timing of the magnetic field control until the measured radiation dose achieves a predetermined value.

15. The treatment method of claim 14, wherein the timing between the tracking and the magnetic filed control is less than 1 ms.

16. A non-transitory computer-readable storage medium upon which is embodied a sequence of programmed instructions for controlling a treatment system to irradiate a treatment volume within a subject along an irradiation axis, and a computer processing system which executes the sequence of programmed instructions embodied on the computer-readable storage medium to cause the computer processing system to:

send a signal to the treatment system to generate a radiation beam and to irradiate a subject disposed on a support system with the radiation beam, the irradiation causing generation of secondary electrons within the subject;

send a signal to a magnetic field control system to:
  apply magnetic fields to the radiation beam; and
  direct the secondary electrons that exit the subject back into the treatment volume using the magnetic fields;

determine a total radiation dose received by the treatment volume, the total radiation dose including radiation dose generated by the redirected secondary electrons; and adjust the irradiation axis and/or a spot size of the radiation beam based on the determined total radiation dose.

17. The non-transitory computer-readable storage medium of claim 16, wherein the computer processing system is further configured to send a signal to a control system to track the treatment volume.

18. The non-transitory computer-readable storage medium of claim 17, wherein the computer processing system is further configured to:

control a laser-driven accelerator system responsively to a location or movement of the tracked treatment volume;

coordinate timing of the application of the magnetic fields; and coordinate timing of the radiation beam generation, the irradiation of the subject, the tracking of the treatment volume, and the total radiation dose determination.

19. The non-transitory computer-readable storage medium of claim 18, wherein the computer processing system is further configured to repeat the generating of the radiation beam, the tracking of the treatment volume, and magnetic field control until the measured radiation dose achieves a predetermined value.

20. The non-transitory computer-readable storage medium of claim 19, wherein the timing between the tracking and the magnetic filed control is less than 1 ms.

\* \* \* \* \*